(12) United States Patent
Li et al.

(10) Patent No.: US 8,343,750 B2
(45) Date of Patent: Jan. 1, 2013

(54) OCHROBACTRUM SP. FOR DEGRADING TETRABROMOBISPHENOL-A (TBBPA) AND ITS APPLICATION

(75) Inventors: Guiying Li, Guangzhou (CN); Taicheng An, Guangzhou (CN); Lei Zu, Guangzhou (CN)

(73) Assignee: Guangzhou Institute of Geochemistry, Chinese Academy of Science, Guangzhou (CN)

( * ) Notice: Subject to any disclaimer, the term of this patent is extended or adjusted under 35 U.S.C. 154(b) by 132 days.

(21) Appl. No.: 12/995,567

(22) PCT Filed: Dec. 30, 2009

(86) PCT No.: PCT/CN2009/076274
§ 371 (c)(1),
(2), (4) Date: Dec. 1, 2010

(87) PCT Pub. No.: WO2011/069310
PCT Pub. Date: Jun. 16, 2011

(65) Prior Publication Data
US 2011/0281332 A1    Nov. 17, 2011

(30) Foreign Application Priority Data

Dec. 11, 2009  (CN) .......................... 2009 1 0213746

(51) Int. Cl.
*C12N 1/20*  (2006.01)
*C12S 99/00*  (2010.01)

(52) U.S. Cl. .................................. 435/252.1; 435/262.5
(58) Field of Classification Search ............... 435/252.1, 435/262.5
See application file for complete search history.

(56) References Cited

FOREIGN PATENT DOCUMENTS

| | | |
|---|---|---|
| CN | 101294140 | 10/2008 |
| CN | 101338284 | 1/2009 |
| JP | 2008-194023 | 8/2008 |

OTHER PUBLICATIONS

Liu Xianjun et al., "Study on isolation and degradation characters of a bacterial strain for aniline degradation," Chinese Journal of Environmental Engineering, vol. 2, No. 6 (Jun. 30, 2008) p. 858-860.
International Search Report for international application No. PCT/CN2009/076274, dated Aug. 19, 2010 (7 pages).

*Primary Examiner* — Chih-Min Kam
(74) *Attorney, Agent, or Firm* — Hamre, Schumann, Mueller & Larson, P.C.

(57) ABSTRACT

The invention discloses an *Ochrobactrum* sp. for degrading TBBPA and its application in environmental remediation. An *Ochrobactrum* sp. for degrading TBBPA was isolated from the sludge in a high risk area of electronic waste in the invention. The strain is named as *Ochrobactrum* sp. T, which has been deposited in China Center for Type Culture Collection (CCTCC) on Oct. 28, 2009 with an accession number of CCTCC M209246. *Ochrobactrum* sp. T obtained in the invention has high degradation capability to TBBPA in environment. The degradation efficiency of the strain achieves 96.2%. The strain could be applied to degrading TBBPA in environmental remediation.

3 Claims, 1 Drawing Sheet

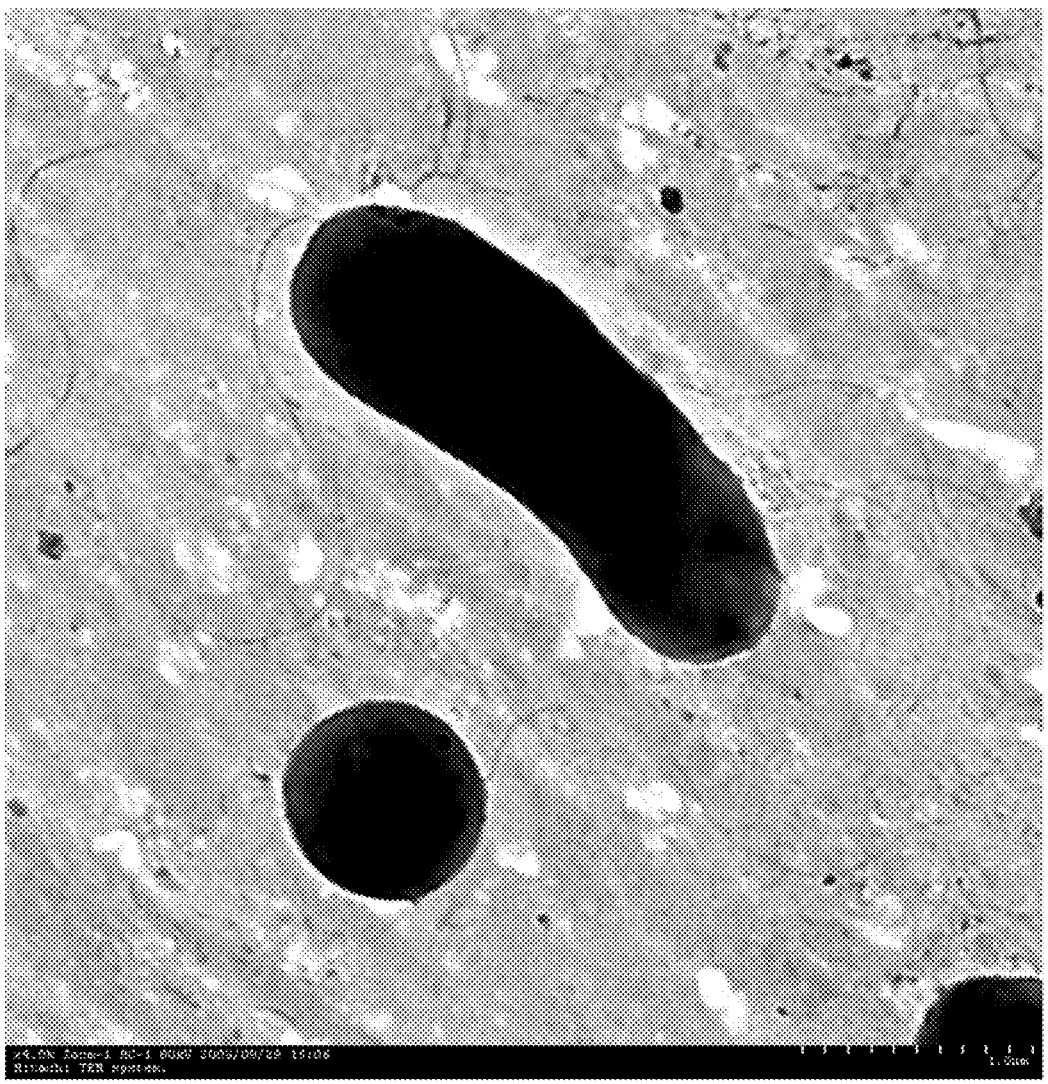

OCHROBACTRUM SP. FOR DEGRADING TETRABROMOBISPHENOL-A (TBBPA) AND ITS APPLICATION

This application is a 371 national stage of PCT/CN76274, filed Dec. 30, 2009.

TECHNICAL FIELD

The present invention belongs to the domain of microorganism technology, and in detail especially relates to an *Ochrobactrum* sp. for degrading TBBPA and its application in environmental remediation.

BACKGROUND ART

Brominated flame retardants (BFRs) are liable to accumulate in human body as well as animal body owing to its characteristics, such as higher persistence, lipophilicity, environmental stability, poor degradability, biomagnification and so on. And BFRs could be concentrated via food chain to poison organisms in high trophic level, eventually endanger human health. The degradation of BFRs in nature has been noticed at abroad. Recent studies indicated that various BFRs could be photolyzed or biodegraded under certain conditions, and dominant microorganisms isolated from the polluted local environment could remove BFRs in environment effectively.

TBBPA is one kind of typical BFRs. The biodegradation of TBBPA has therefore become a focus of hot research. Moreover, *Ochrobactrum* sp. is a new genus established by Holmes et al. in 1988. The characteristics of this strain are as follows: it is an obligate aerobe; the Gram-reaction is negative while the oxidase and catalase reactions are positive; and it can't hydrolyze gelatin. The strain has the ability of utilizing different kinds of amino acid, organic acid or carbohydrate as carbon sources. An *Ochrobactrum* sp. capable of degrading TBBPA has not been isolated up to date.

DISCLOSURE OF THE INVENTION

To overcome the defects and shortages in the art, the first one object of the present invention is to provide an *Ochrobactrum* sp. for degrading TBBPA.

Another object of the present invention is to provide the application of *Ochrobactrum* sp. for degrading TBBPA.

The object of the present invention is realized by the undermentioned technical proposal: an *Ochrobactrm* sp. for degrading TBBPA being named as *Ochrobactmm* sp. T, which has been deposited in China Center for Type Culture Collection (CCTCC), Luo-jia-shan, Wuchang, Wuhan 430072, Hubei Province, P.R. China, on Oct. 28, 2009 with an accession number of CCTCC M209246, where the deposited culture is a pure culture.

The *Ochrobactrum* sp. for degrading TBBPA was obtained, its appearance as well as physiological and biochemical characteristics are as follows:

Its appearance characteristics are as follows:

a. The isolated *Ochrobactrum* sp. is observed by physiological and biochemical identification method as well as electron microscope, the result is as follows: the strain is a Gram-negative, rod shaped and rounded end measuring 0.4-0.8×1.6-2.2 µm with peritrichous flagella;

b. The appearance characteristics of the strain colonies are as follows: after culturing 24 h on LB agar culture medium, colonial morphology of the strain becomes roundness, colourless, transparence, and colony diameter is 1~2 mm;

c. The main biochemical characteristics are as follows: it is a obligate aerobe possessing strict respiratory metabolism, catalase and oxidase reaction are positive, its indole test is negative and can not hydrolyze gelatin, stab inoculation movement is negative on semisolid LB culture medium.

The said *Ochrobactrum* sp. for degrading TBBPA has 16S rRNA sequence represented by SEQ. ID. NO:1.

The said *Ochrobactrum* sp. for degrading TBBPA can be used in environmental remediation. It can be used in degrading TBBPA in environment, such as atmosphere, waters or soil.

Relative to the art, advantages and beneficial effects of the present invention lie in:

(1) An *Ochrobactrum* sp. for degrading TBBPA was isolated from the soil in Guiyu region, Guangdong province (a world largest electronic waste dismantling site) in the invention for the first time.

(2) *Ochrobactrum* sp. obtained in the invention has high degradation capability to TBBPA. The degradation efficiency of the strain achieves 96.2% within 84 h in the condition that the substrate concentration is 2 mg/L.

BRIEF DESCRIPTION OF DRAWINGS

FIG. 1 is a form image of *Ochrobactrum* sp. T in the present invention by the transmission electron microscope.

DETAILED DESCRIPTION OF THE INVENTION

The invention is further illustrated by the following examples as well as the drawings, which are not to be construed in any way as imposing limitations upon the scope thereof.

Example 1

An *Ochrobactrum* sp. for degrading TBBPA in the invention was isolated and purified from the sludge in electronic waste recycling area Guiyu town, Guangdong province, China. The isolation and purification means are as follows: isolation culture medium used in the experiment is mineral medium (g/L) ($K_2HPO_4$ 4.35, $KH_2PO_4$ 1.70, $NH_4NO_3$ 2.10, $MgSO_4$ 0.20, $MnSO_4$ 0.05, $FeSO_4 \cdot 7H_2O$ 0.01, $CaCl_2 \cdot 2H_2O$ 0.03). Firstly, three gram of sludge was added into the mineral medium containing 10 mg/L TBBPA, and cultured for 7 days at 37° C. And then the culture is inoculated into the mineral medium containing 20 mg/L TBBPA with 5% inoculum concentration for another week. The concentration of TBBPA was gradually increased by analogy to go on cultivation, as the concentration used is 30 mg/L, 40 mg/L and 50 mg/L, respectively. After acclimatization, the culture is inoculated into the beef extract and peptone liquid medium (beef extract 3.0 g/L, peptone 10.0 g/L, NaCl 5.0 g/L, pH7.4-7.6) with 5% inoculum concentration for culturing 12 h. A 0.1 ml of bacterium suspension (diluted to $10^{-1}$~$10^{-7}$) is spread on solid agar plate containing 10 mg/L TBBPA which is the sole carbon source ($K_2HPO_4$ 4.35 g/L, $KH_2PO_4$ 1.70 g/L, $NH_4NO_3$ 2.10 g/L, $MgSO_4$ 0.20 g/L, $MnSO_4$ 0.05 g/L, $FeSO_4 \cdot 7H_2O$ 0.01 g/L, $CaCl_2 \cdot 2H_2O$ 0.03 g/L, agar powder 1.80 g/L) until single colony appears on the plate. The colonies of fast growth and regular fringe are picked out as the pure bacterium.

The colony picked out is identified, and the result is as follows:

(1) Its appearance characteristics are as follows:

a. The isolated strain *Ochrobactrum* sp. was identified by physiological and biochemical characterization as well as the transmission electron microscope observation, the result is as follows: the strain is Gram-negative, it is bacilliform under the transmission electron microscope, cell size is 0.4~0.8× 1.6~2.2 μm, peritrichous, as shown in FIG. 1;

b. The appearance characteristics of the strain are as follows: After culturing 24 h in LB solid culture medium, the colonial morphology is round, colourless, transparent, and colonial diameter is 1~2 mm;

c. The main physiological and biochemical characteristics are as follows: obligate aerobic, strict respiratory metabolism, catalase and oxidase positive, indole test negative, without hydrolyzing gelatin, stab inoculation movement negative on semisolid LB culture medium.

The above result indicates that the strain obtained in the invention is similar, to *Ochmbactrum* sp. in physiological and biochemical characteristic.

(2) Total DNA of the stain is extracted via thermal denaturation method. Universal primer is applied to amplify 16S rRNA of the bacteria, and the result of sequencing is as follows (SEQ ID: No. 1):

```
tggagccgtg tcgacagcct accatgcagt cgagcgcgta gcaatacgag cggcagacgg    60
gtgagtaacg cgtgggaatc tacccatcac tagggaataa ctcagggaaa cttgtgctaa   120
taccctatac gaccgagagg tgaaagattt atcggtgatg gatgagcccg cgttggatta   180
gctagttggt ggggtaaagg cctaccaagg cgacgatcca tagctggtct gagaggatga   240
tcagccacac tgggactgag acacggccca gactcctacg ggaggcagca gtggggaata   300
ttggacaatg ggcgcaagcc tgatccagcc atgccgcgtg agtgatgaag ccctagggt    360
tgtaaagctc tttcaccggt gaagataatg acggtaaccg gagaagaagc cccggctaac   420
ttcgtgccag cagccgcggt aatacgaagg gggctagcgt tgttcggatt tactgggcgt   480
aaagcgcacg taggcgggct aataagtcag gggtgaaatc ccggggctca accccggaac   540
tgcctttgat actgttagtc ttgagtatgg aagaggtgag tggaattccg agtgtagagg   600
tgaaattcgt agatattcgg aggaacacca gtggcgaagg cgggctcact ggtgcattac   660
tgacgctgag gtgcgaaagc gtggggagca aacaggatt agataccctg ggtagtccac   720
gccgtaatcg atgaatgtta gccgttgggg agtttactct tcggtggcgc agctaacgca   780
ttaaacattc cgcctgggga gtacggtcgc aagattaaaa ctcaaaggaa ttgacggggg   840
cccgcacaag cggtggagca tgtggtttaa ttcgaagcaa cgcgcagaac cttaccagcc   900
cttgacatcc cgatcgcggt tagtggagac actttccttc agttcggctg gatcggagac   960
aggtgctgca tggctgtcgt cagctcgtgt cgtgagatgt tgggttaagt cccgcaacga  1020
gcgcaaccct cgcccttagt tgccagcatt cagttgggca ctctaagggg actgccggtg  1080
ataagccgag aggaaggtgg ggatgacgtc aagtcctcat ggcccttacg ggctgggcta  1140
cacacgtgct acaatggtgg tgacagtggg cagcgagcac gcgagtgtga gctaatctcc  1200
aaaagccatc tcagttcgga ttgcactctg caactcgagt gcatgaagtt ggaatcgcta  1260
gtaatcgcgg atcagcatgc cgcggtgaat acgttcccgg gccttgtaca caccgcccgt  1320
cacaccatgg gagttggttt tacccgaagg cgctgtgcta accgcaagga ggcacgcgac  1380
cacggtaggg tcagcgatct ggcgtgaagt cggaaccaaa gttttagggg gc           1432
```

The sequence of 16S rRNA is 1432 bp length. Compared with the gene sequence accessed in GenBank, it can be found that the strain is with a homology of 98.1% to *Ochrobactrum* sp. CGL-x and a homology of 96.2% to *Ochrobactrum* intermodium CCUG 2469T which is the most similar type strain to the strain of the present invention.

According to the above physiological and biochemical characteristics as well as the result of 16S rRNA sequence comparison, the strain obtained in the invention should be classified to *Ochrobactrum* sp. Moreover, it should be new species in the said genus, which is named as *Ochrobactrum* sp. T.

The said strain has been deposited in China Center for Type Culture Collection (CCTCC) on Oct. 28, 2009 with an accession number of CCTCC M209246.

Example 2

The *Ochrobaoctrum* sp. T obtained in the invention has high degradation capability to TBBPA:

4.35 g $K_2HPO_4$, 1.70 g $KH_2PO_4$, 2.10 g $NH_4NO_3$, 0.20 g $MgSO_4$, 0.05 g $MnSO_4$, 0.01 g $FeSO_4.7H_2O$, 0.03 g $CaCl_2.2H_2O$ are added into 1 L de-ionized water. 100 ml of culture medium is transferred into 250 ml shake flasks, sterilized for 30 min at 121° C., and then taken out. Different concentrations of TBBPA are incorporated into culture medium under aseptic condition. The concentrations of TBBPA are 2 mg/L, 5 mg/L, 10 mg/L, 15 mg/L, 20 mg/L, and 25 mg/L, respectively. *Ochrobactrum* sp. T preserved on the agar slant is inoculated into LB culture medium and activated in incubator of 220 r/min at 30° C. for 15 h. Then the culture inoculated into the mineral medium containing TBBPA with inoculum concentration of 5%. TBBPA was degraded at 30° C. and the degradation efficiency was determined by High Performance Liquid Chromatography (HPLC). The detected condition of HPLC is as follows: 80% methanol, 18% ultra-pure water, 2% acetic acid at the flow rate is 1 ml/min and detection wavelength of TBBPA is 210 nm. Degradation efficiency is measured after 84 h treatment at different initial concentrations of TBBPA, the result is shown in Table 1:

TABLE 1

Degradation efficiency of TBBPA in different initial concentrations

| Concentration of TBBPA | Degradation efficiency |
| --- | --- |
| 2 mg/L | 96.2% |
| 5 mg/L | 74.9% |
| 10 mg/L | 68.4% |
| 15 mg/L | 63.1% |

TABLE 1-continued

Degradation efficiency of TBBPA in different initial concentrations

| Concentration of TBBPA | Degradation efficiency |
| --- | --- |
| 20 mg/L | 55.7% |
| 25 mg/L | 41.3% |

From Table 1, it can be seen that *Ochrobactrum* sp. T obtained in the invention has high degradation capability to TBBPA in environment. The degradation efficiency of the strain achieves 96.2% at the TBBPA concentration of 2 mg/L.

The above specific implementation examples are prefer embodiments of the present invention. However, they shall not be taken as the limitation to the present invention. All revision, modification, replacement, combination and reduction that come within the technical meaning and range of equivalency of the present invention are all equivalent substitute modes, and intended to be embraced therein.

What is claimed is:

1. An isolated *Ochrobactrum* sp. that degrades tetrabromobisphenol-A (TBBPA) being named as *Ochrobactrum* sp. T, which has been deposited in China Center for Type Culture Collection (CCTCC) with an accession number of CCTCC M209246.

2. A method of degrading tetrabromobisphenol-A (TBBPA) in an environmental medium, comprising: purifying the environmental medium with an amount of the *Ochrobactrum* sp. T of claim 1 effective for degrading the TBBPA.

3. The method of claim 2, wherein the environmental medium is at least one selected from the group consisting of atmosphere, water and soil.

* * * * *

SEQUENCE LISTING

```
<160> NUMBER OF SEQ ID NOS: 1

<210> SEQ ID NO 1
<211> LENGTH: 1432
<212> TYPE: DNA
<213> ORGANISM: Ochrobactrum sp.

<400> SEQUENCE: 1
tggagccgtg tcgacagcct accatgcagt cgagcgcgta gcaatacgag cggcagacgg      60
gtgagtaacg cgtgggaatc tacccatcac tagggaataa ctcagggaaa cttgtgctaa     120 tacccatatac gaccgagagg tgaaagattt atcggtgatg gatgagcccg cgttggatta    180
gctagttggt ggggtaaagg cctaccaagg cgacgatcca tagctggtct gagaggatga    240
tcagccacac tgggactgag acacggccca gactcctacg ggaggcagca gtggggaata    300
ttggacaatg ggcgcaagcc tgatccagcc atgccgcgtg agtgatgaag gccctagggt    360
tgtaaagctc tttcaccggt gaagataatg acggtaaccg gagaagaagc cccggctaac    420
ttcgtgccag cagccgcggt aatacgaagg gggctagcgt tgttcggatt tactgggcgt    480
aaagcgcacg taggcgggct aataagtcag gggtgaaatc ccggggctca accccggaac    540
tgcctttgat actgttagtc ttgagtatgg aagaggtgag tggaattccg agtgtagagg    600
tgaaattcgt agatattcgg aggaacacca gtggcgaagg cgggctcact ggtgcattac    660
tgacgctgag gtgcgaaagc gtggggagca aaacaggatt agataccctg ggtagtccac    720
gccgtaatcg atgaatgtta gccgttgggg agtttactct tcggtggcgc agctaacgca    780
ttaaacattc cgcctgggga gtacggtcgc aagattaaaa ctcaaaggaa ttgacggggg    840
cccgcacaag cggtggagca tgtggtttaa ttcgaagcaa cgcgcagaac cttaccagcc    900
cttgacatcc cgatcgcggt tagtggagac actttccttc agttcggctg gatcggagac    960
aggtgctgca tggctgtcgt cagctcgtgt cgtgagatgt tgggttaagt cccgcaacga   1020
gcgcaaccct cgcccttagt tgccagcatt cagttgggca ctctaagggg actgccggtg   1080
ataagccgag aggaaggtgg ggatgacgtc aagtcctcat ggcccttacg ggctgggcta   1140
```

```
cacacgtgct acaatggtgg tgacagtggg cagcgagcac gcgagtgtga gctaatctcc    1200
aaaagccatc tcagttcgga ttgcactctg caactcgagt gcatgaagtt ggaatcgcta    1260
gtaatcgcgg atcagcatgc cgcggtgaat acgttcccgg gccttgtaca caccgcccgt    1320
cacaccatgg gagttggttt tacccgaagg cgctgtgcta accgcaagga ggcacgcgac    1380
cacggtaggg tcagcgatct ggcgtgaagt cggaaccaaa gttttagggg gc            1432
```